United States Patent [19]

Shinitzky et al.

[11] Patent Number: 5,602,164
[45] Date of Patent: Feb. 11, 1997

[54] ANTI-OBESITY DRUGS

[75] Inventors: Meir Shinitzky, Kfar Shmaryahu; Avner Shenfeld, Rehovot, both of Israel

[73] Assignee: Senyorina Ltd., Kfar Shmaryahu, Israel

[21] Appl. No.: 616,948

[22] Filed: Mar. 18, 1996

Related U.S. Application Data

[63] Continuation of Ser. No. 524,961, Sep. 8, 1995, which is a continuation-in-part of Ser. No. 325,422, Dec. 19, 1994, abandoned.

[30] Foreign Application Priority Data

Apr. 28, 1992 [IL] Israel ......................... 101708

[51] Int. Cl.$^6$ ................ A61K 31/415; A61K 31/40; A61K 31/235; A61K 31/24
[52] U.S. Cl. ................ 514/400; 514/419; 514/423; 514/532; 514/538; 514/547; 514/549; 514/550; 514/551; 514/556; 514/617; 514/619; 514/621; 514/626; 514/627; 514/909
[58] Field of Search ................ 514/400, 419, 514/423, 532, 538, 547, 549, 550, 551, 556, 617, 619, 621, 626, 627, 909

[56] References Cited

U.S. PATENT DOCUMENTS

| | | | |
|---|---|---|---|
| 4,634,795 | 1/1987 | Bar-Tana | 562/590 |
| 4,689,344 | 8/1987 | Bar-Tana | 514/527 |
| 4,711,896 | 12/1987 | Bar-Tana et al. | 514/570 |
| 4,908,385 | 3/1990 | Bar-Tana et al. | 514/574 |

OTHER PUBLICATIONS

J. Bar–Tana, et al., Inhibition of Lipid Synthesis by ββ'–Tetramethyl–Substituted, $C_{14}$–$C_{22}$, ∝,w–Dicarboxylic Acids in the Rat In Vivo*, vol. 260, No. 14, pp. 8404–8410, 1985.

G. Rose–Kahn, et al., Inhibition of Lipid Syntesis by ββ–Tetramethyl–Substituted, $C_{14}$–$C_{22}$, ∝, w–Dicarboxylic Acids in Cultured Rat Hepatocytes*, vol. 260, No. 14, pp. 8411–8415.

J. Bar–Tana, et al., Hypolipidemic Effect of β,β–Methyl–Substituted Hexadecanedioic Acid (MEDICA 16) in Normal and Nephro Rats, vol. 29, pp. 431–441, 1988.

B. Frenkel, et al., The Hypochylomicronemic Effect of β,β–Methyl Substituted Hexadecanedioic Acid (MEDICA 16) Is Mediated by a Decrease in Apolipoprotein C–III*, vol. 263, No. 17, pp. 8491–8497, 1988.

R. Tzur, et al., Hypolipidemic, Antiobesity, and Hypoglycemic–Hypoinsulinemic Effects of β,β'–Methyl–Substituted Hexadecanedioi Acid in Sand Rats, vol. 37, pp. 1618–1624, Dec.–1988.

*Primary Examiner*—Kimberly Jordan
*Attorney, Agent, or Firm*—Sprung Horn Kramer & Woods

[57] ABSTRACT

Obesity is treated by the administration to a subject of a compound having the general formula (I): $R_4$—$(CH_2)_n$—CO—$N(R_1)$—$CH(R_2)$—CO(—$R_3$), wherein $R_1$ represents H or $CH_3$; $R_2$ represents a side chain of a naturally occurring amino acid; $R_3$ represents OH, $OCH_2CH_3$ and $NH_2$; n is 6–18; and $R_4$ represents $CH_3$ or a group having the general formula (II): $R_3$—CO—$CH(R_2)$—$N(R_1)$—CO—, wherein $R_1$, $R_2$ and $R_3$ have the above meanings. The compounds of formula (I) wherein $R_4$ is a group of formula (II), are novel compounds.

2 Claims, 4 Drawing Sheets

ANTI-OBESITY DRUGS

CROSS-REFERENCES TO RELATED APPLICATIONS

This application is a continuation of application Ser. No. 08/524,961, filed Sep. 8, 1995, now pending, which is a continuation of application Ser. No. 325,422, filed Dec. 19, 1994, now abandoned.

FIELD OF THE INVENTION

The present invention is in the field of treatment and prevention of obesity. The present invention provides compositions and methods for the treatment or prevention of such disorders utilizing, as active ingredient, lypophilic derivatives of natural amine acids. Furthermore, the present invention provides certain such novel compounds.

PRIOR ART

The following prier art is believed to be relevant as a background to the present invention:

1. Bar-Tana et al., *J. Biol. Chem.*, 1985, 260, 8404–8410.
2. Rose-Kakn et al., *J. Biol. Chem.*, 1985, 260, 8411–8415.
3. Bar-Tana et al., *J. Lipid Res.*, 1988, 29, 431–441.
4. Frenkel et al., *J. Biol. Chem.*, 1988, 263, 8491–8497.
5. Tzur et al., *Diabetes*, 1988, 37, 1618–1624.
6. U.S. Pat. No. 4,634,795.
7. U.S. Pat. No. 4,689,344.
8. U.S. Pat. No. 4,711,896.
9. U.S. Pat. No. 4,908,385.

In the following text, reference to these prior an publications will be made by indicating in brackets their number from the above list.

BACKGROUND OF THE INVENTION

Energy from food is primarily provided by carbohydrates and lipids. Carbohydrates usually supply the immediate energy needs and their excess is stored as glycogen in the liver or converted to lipids. Lipids can also be metabolized as immediate energy providing substances but their rate of energy provision is relatively slow and they are generally stored in the body for use in states of deprivation. Lipid is stored in the body mostly as fat under the skin and consumption of lipids and carbohydrates beyond the metabolic need leads to fattening. The associated medical and aesthetic problems, are a major concern in modem society.

Apart from surgery and dietary means for reduction of fat absorption in the small intestine, there are presently no satisfactory, means for reducing fat storage in the body and the current means of choice are still diet and exercise. There is, however, a desire for drugs which will reduce fat accumulation by inhibiting lipid and lipoprotein synthesis in the liver. Recently, a series of $\beta,\beta'$ tetramethyl substituted $\alpha,\omega$ dicarboxylic acids (MEDICA) have been synthesized and suggested as potential anti-fattening drugs[1–4,6–9]. The most potent drug of this series was found to be the hexadecane derivative (MEDICA 16). It was demonstrated that MEDICA, which is a non-naturally occurring fatty acid, could inhibit biosynthetic pathways of triglycerides and cholesterol in the liver. Experiments with MEDICA 16 given in the diet to normal and obese rats have indicated a strong inhibition of glyceride and cholesterol biosynthesis in the liver evidenced by a marked reduction in their serum contents[3]. Furthermore, in the obese animals adipose tissue was reduced by about 75% over the whole body concomitantly to extensive weight loss[5]. However, the metabolic clearance of these compounds via integration into glycerol esters or via oxidation is relatively slow due to the presence of carboxylate at the two edges of the molecules and the $\beta$ alkyl substitution. Despite their impressive effect, MEDICA are expected to exert a long term toxicity due to their non-compatible molecular structure. Thus, chronic intake of MEDICA, which is required for maintaining a low fat state, would likely be associated with adverse toxic effects in the long run.

OBJECTS OF THE INVENTION

It is the object of the present invention to provide a pharmaceutical composition, method and dietary supplements for the treatment and/or prevention of obesity. More specifically, it is an object of the present invention to provide such composition and method utilizing lipophilic derivatives of natural amino acids.

It is a further object of the present invention to provide certain novel lipophilic derivatives of natural amino acids useful in such compositions and methods.

The remaining objects of the present invention will be illustrated from the following description and claims.

GENERAL DESCRIPTION OF THE INVENTION

By a first of its aspects, the present invention provides a pharmaceutical composition for the treatment of obesity comprising a pharmaceutically acceptable career and, as an active ingredient, a compound having the general Formula I:

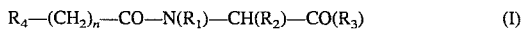

$$R_4-(CH_2)_n-CO-N(R_1)-CH(R_2)-CO(R_3) \quad (I)$$

wherein $R_1$ represents H or $CH_3$ $R_2$ represents a side chain of a naturally occurring amino acid;

$R_3$ represents OH, $OCH_2CH_3$ and $NH_2$;

n is 6–18, preferably 12–16; and $R_4$ represents $CH_3$ or a group having the general Formula II:

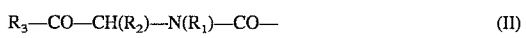

$$R_3-CO-CH(R_2)-N(R_1)-CO- \quad (II)$$

wherein $R_1$, $R_2$ and $R_3$ have the above meanings.

The present invention also provides methods for the treatment of obesity comprising administering to a subject in need an effective amount of an active ingredient being a compound having the general Formula I as defined above.

The present invention also provides a dietary supplement for the prevention of obesity comprising an active ingredient being a compound of the general Formula I as defined above.

The compounds according to Formula I wherein $R_4$ represents a group of Formula II are novel, and such compounds are also provided by the present invention.

An example of compounds of Formula I wherein $R_4$ is $CH_3$, is N-palmitoyl sarcosine (P-Sat) having the Formula III:

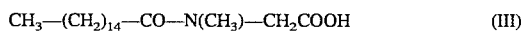

$$CH_3-(CH_2)_{14}-CO-N(CH_3)-CH_2COOH \quad (III)$$

Examples of compounds of Formula I, in which $R_4$ represents a group having the general Formula II, are N,N' sebacoyl bis-glycine (GSG), having the Formul IV:

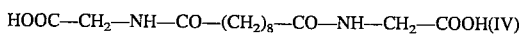
$$HOOC-CH_2-NH-CO-(CH_2)_8-CO-NH-CH_2-COOH \quad (IV)$$

N,N' sebacoyl bis 1-aspargin (NSN), having the Formula V:

$$(CH_2)_8-[CO-NH-CH(CH_2CONH_2)-COOH]_2 \quad (V)$$

N,N' sebacoyl bis-sarcosine [S(Sar)$_2$]having the Formula VI:

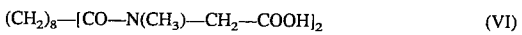
$$(CH_2)_8-[CO-N(CH_3)-CH_2-COOH]_2 \quad (VI)$$

N,N' sebacoyl bis-sarcosine-ethylester [S(SarOEt)$_2$], having the Formula VII:

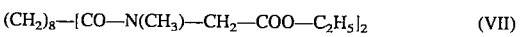
$$(CH_2)_8-[CO-N(CH_3)-CH_2-COO-C_2H_5]_2 \quad (VII)$$

and

N,N' sebacoyl bis-phenylalanine (FSF), having the Formula VIII:

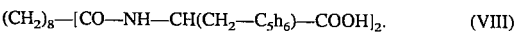
$$(CH_2)_8-[CO-NH-CH(CH_2-C_5h_6)-COOH]_2. \quad (VIII)$$

The present invention will now be described with reference to the following non-limiting examples.

EXAMPLE 1 preparation of compounds

Lypophilic derivatives of the natural amino acids can be synthesized via the N-hydroxy succinimide ester of the respective fatty acid. Such active esters react with primary or secondary amine to form the corresponding amide while liberating a free N-hydroxy succinimide.

In the following are three examples of such synthesis:

A: preparation of P-Sar

Hydroxy succinimide ester of palmitic acid (PHS) was obtained from SIGMA. One volume of 30 mM PHS in tetrahydrofuran was mixed with one volume of excess sarcosine (0.3M) in 0.1M of aqueous sodium bicarbonate according to the procedure described by Lapidot et al., *J. Lipids Res.*, 1967, 8, 142. The mixture was mixed at 40° C. for 24 hours. The tetrahydrofuran was then evaporated-and the mixture was acidified to pH 1 with HCl, whereupon the crude product precipitated and was collected. After washing with water the product was crystallized from isopropanol.

B: preparation of GSG (a) 1 mole of sebacic acid was reacted with 2 moles of N-hydroxysuccinimide and 2 moles of dicyclohexyl carbondiimide in ethyl acetate. The resulting compound, 1,10 sebacoyl di (N-hydroxysuccinimide) ester, [Seb-(NHS)$_2$] was crystallized from isopropanol. Seb(NHS)$_2$ was found to have an m.p. of 159° C.

(b) 1 volume of 30 mM Seb(NHS)$_2$ in tetrahydrofuran with 1 volume excess glycine (0.3M) in aqueous 0.1M sodium bicarbonate according to the procedure described by Lapidot et al., supra. After 24 hours of mixing at 40° C., the tetrahydrofuran was evaporated under reduced pressure and the product was precipitated by acidifying with 1M HCl to pH 1. The precipitate was collected and washed with water. Crystallization was from isopropanol.

C: preparation of NSN

NSN was prepared by the same procedure of Example (B) except that instead of glycine in step (b), 1-asparagine was used.

The remaining compounds described in the following were prepared in a similar manner, mutatis mutandis.

EXAMPLE 2

Figure 1:
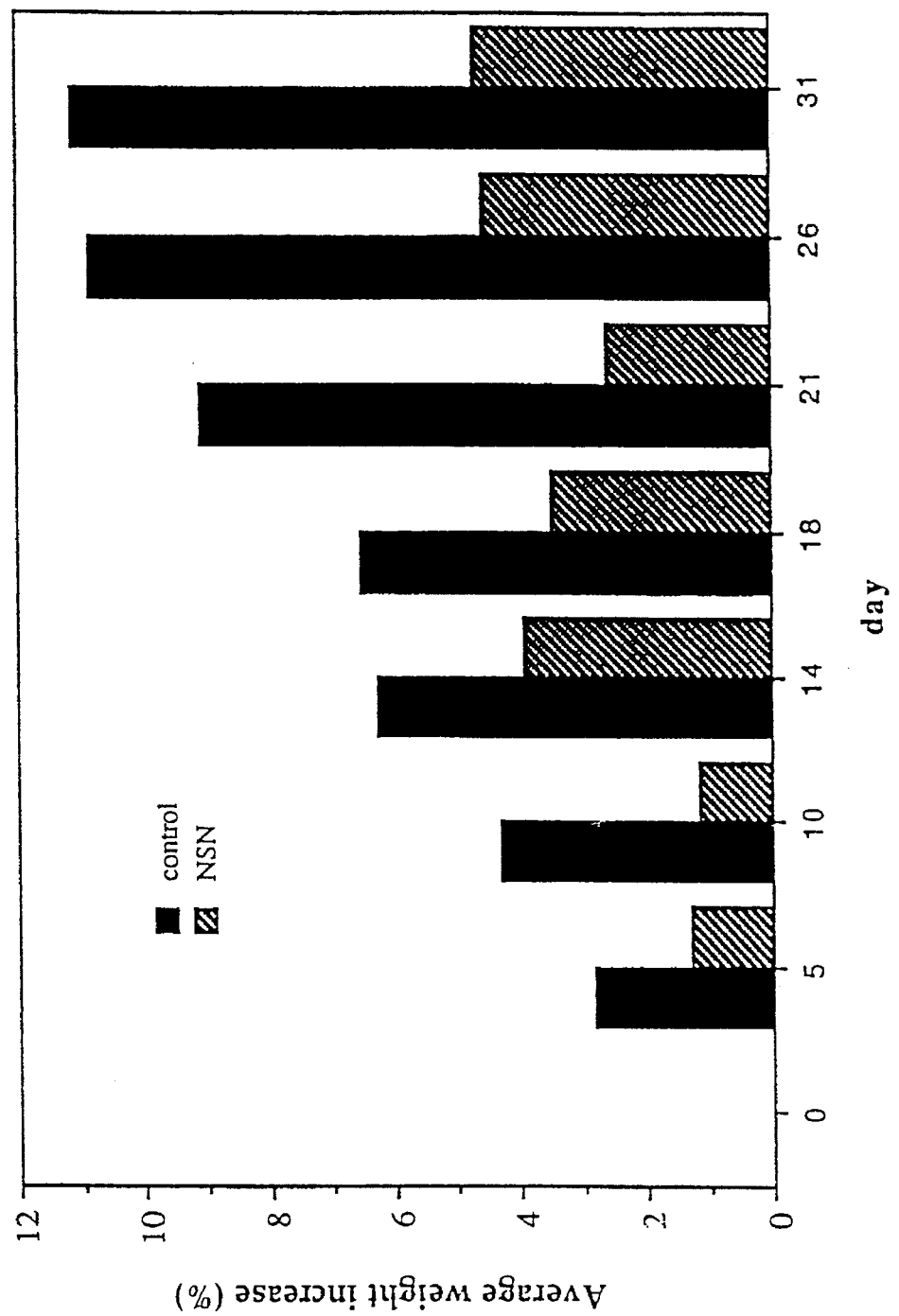
FIG. 1 shows the effect of NSN (0.1% w/w in purina) on weight of 3 months old mice during a 1 month ad lib. feeding.

Experimental results (a) Two groups of 5 three months old mice were fed with purina, ad lib. The diet of 1 group was supplemented with NSN (0.1% w/w in purina). The weight increase of the mice in each group was measured over 31 days and the results shown in FIG. 1 clearly demonstrate that the weight increase of the experimental group, was far less than that in the control group.

(b) 5 groups of 5 three months old mice each, were fed with, a fattening diet consisting of purina and 6% corn oil, and out of these five groups, the diet of four was supplemented with anti-fattening drugs in accordance with the invention (0.1% w/w in the food). The following drugs were tested: P-Sat, GSG, S(Sar)$_2$ and S(SarOEt)$_2$.

Figure 2:
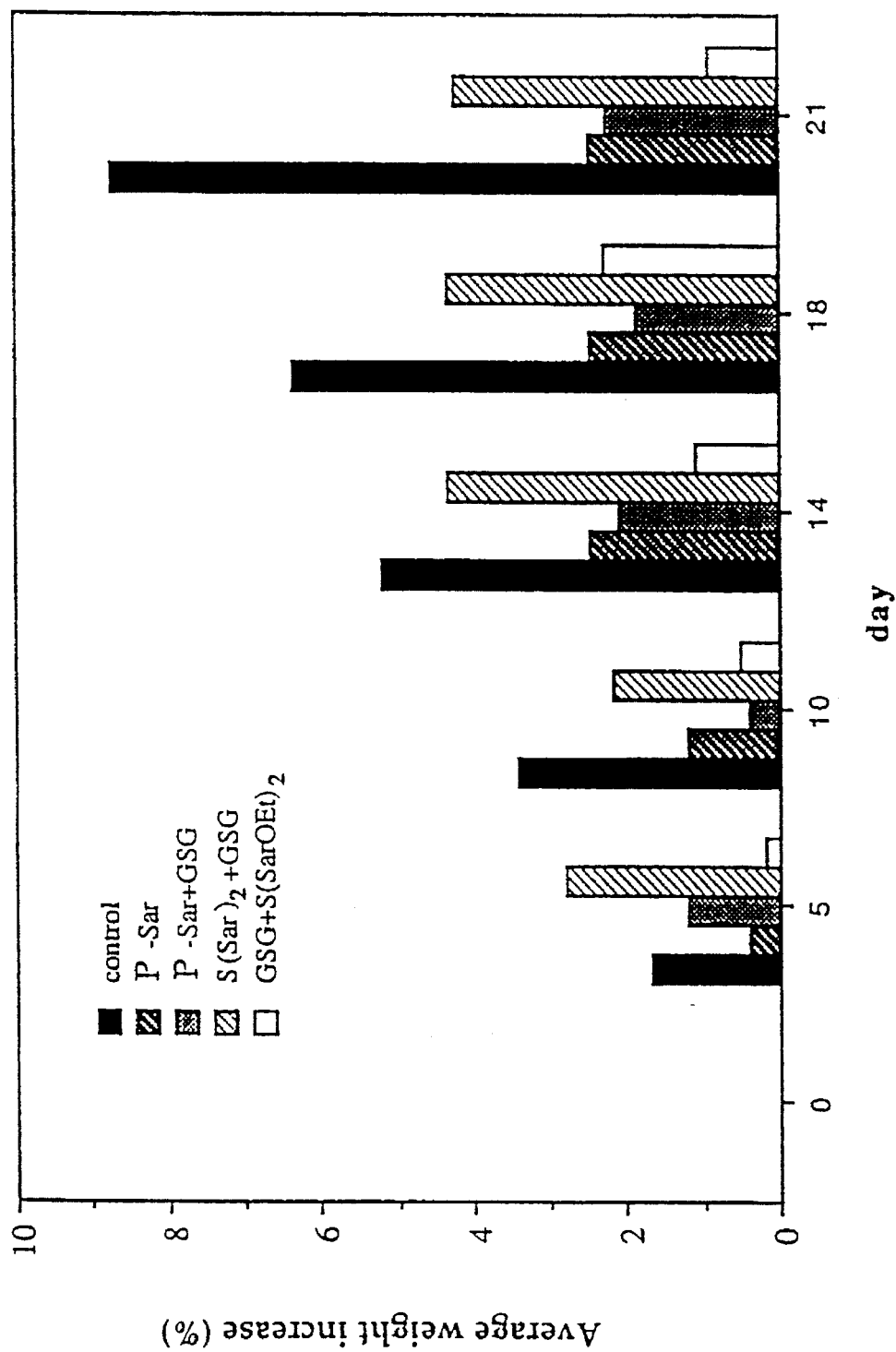
FIG. 2 shows the effect of several anti-fattening agents including a fattening diet in accordance with the invention (0.1% w/w in purina + 6% corn oil) on weight of 3 months old mice.

The results shown in FIG. 2 clearly demonstrate that the weight increase of the treated animals was far less than that of the animals of the control group.

(c) Adult mice were divided into 9 groups of five mice each, and were fed with normal purina ad lib. and 8 groups received one of the following supplements in their diet (0.25% or 0.35% w/w in the food): dNSN, NSN, dlFSF and FSF.

One group did not receive any supplement and served as control.

Food consumption was ad lib.

The treatment was over a period of 40 days after which it was ceased and all groups of animals returned to a normal diet.

Figure 3:
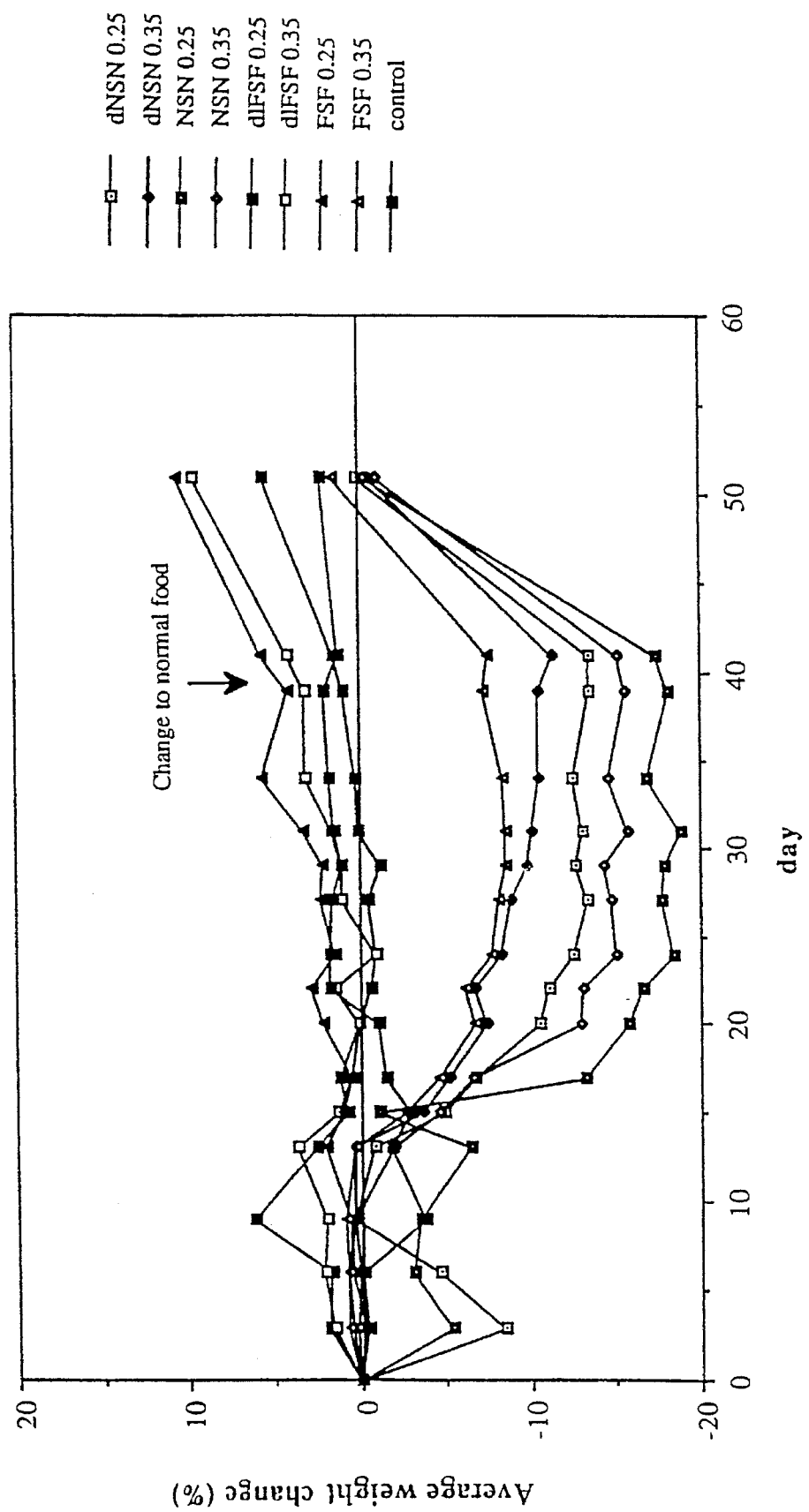
FIG. 3 shows the daily weight of adult mice administered with various anti-fattening agents of the invention.

The results shown in FIG. 3 clearly demonstrate that some of the supplements caused even a slight increase over control. Thus for example, while an increase was observed with 0.25% FSF, a considerable decrease in weight over the entire tested period was observed with 0.35%. FSF. Accordingly it is believed that upon increase of the concentration of these drugs they will all have an anti-fattening affect.

(d) 8–12 months old mice were administered with NSN either intra peritonelly (I.P.) or Per Os (P.O.), 10 mg per day for 4 days. The incorporation of $^3H_2O$ to liver and adipose tissue was tested. For that purpose tritiated water was injected I.P. after overnight fast and 2 hours later the animals were sacrificed and the incorporation into lipids of the liver and the adipose tissue were determined by measuring radioactivity.

Figure 4:
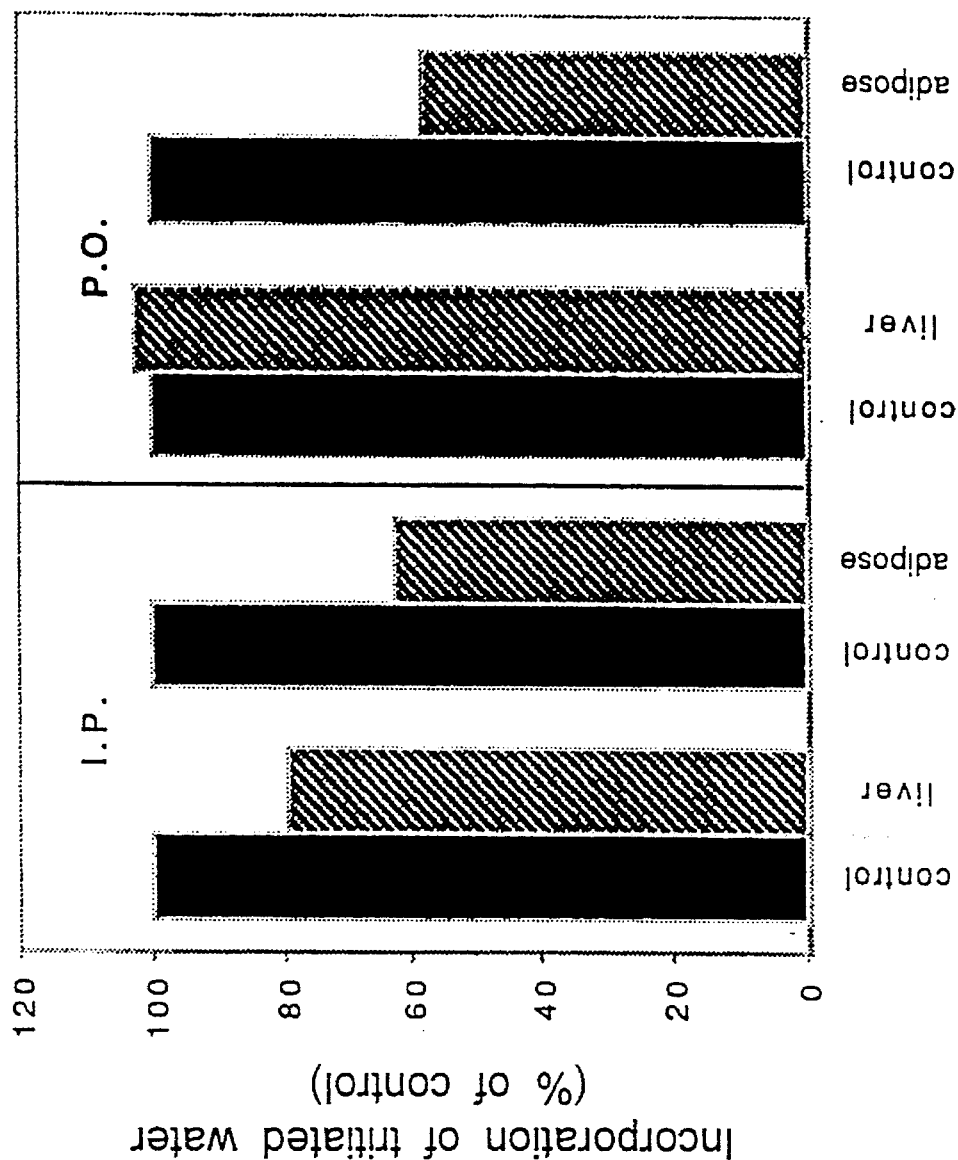
FIG. 4 shows the effect of treatment with NSN on the $^3H_2O$ incorporation to liver and adipose tissue of adult mice.

The results shown in FIG. 4, clearly demonstrate the decrease in treated water incorporation into the treated animals.

We claim:

1. A method of treatment of obesity, comprising administering to an individual in need thereof, an effective amount of an active compound having the general formula I:

$$R_4-(CH_2)_{13}\ CO-N(R_1)-CH(R_2)-CO(-R_3) \quad (I)$$

where
- $R_1$ represents H or $CH_3$;
- $R_2$ represents a side chain of a naturally occurring amino acid;
- $R_3$ represents OH, $OCH_2CH_3$ or $NH_2$;
- n is 6–18 and
- $R_4$ represents $CH_3$ or a group having the feneral Formula II:

$$R_3-CO-CH(R_2)-N(R_1)-CO- \quad (II)$$

where $R_1$, $R_2$ and $R_3$ have the above meanings.

2. A method according to claim 1, wherein in said active compound $R_4$ represents a group of the general formula II:

$$R_3-CO-CH(R_2)-N(R_1)-CO- \quad (II)$$

where $R_1$, $R_2$, and $R_3$ have the meanings as in claim 1.

* * * * *

UNITED STATES PATENT AND TRADEMARK OFFICE
CERTIFICATE OF CORRECTION

PATENT NO. : 5,602,164
DATED : February 11, 1997
INVENTOR(S) : Shinitzky, et al.

It is certified that error appears in the above-indentified patent and that said Letters Patent is hereby corrected as shown below:

Col. 5, line 3    Delete " $R_4-(CH_2)_{13}\ CO-N(R1)-CH(R_2)-CO(-R_3)$ " and substitute -- $R_4-(CH_2)_n-CO-N(R_1)-CH(R_2)-CO(-R_3)$ --

Signed and Sealed this

Twenty-second Day of July, 1997

*Attest:*

*Attesting Officer*

BRUCE LEHMAN

*Commissioner of Patents and Trademarks*